United States Patent
Chavez et al.

(10) Patent No.: US 8,609,880 B1
(45) Date of Patent: *Dec. 17, 2013

(54) PROCESS FOR THE PREPARATION OF AN ENERGETIC NITRATE ESTER

(76) Inventors: David E. Chavez, Ranchos de Taos, NM (US); Darren L. Naud, Los Alamos, NM (US); Michael A. Hiskey, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,419

(22) Filed: Sep. 4, 2012

Related U.S. Application Data

(62) Division of application No. 12/566,331, filed on Sep. 24, 2009, now Pat. No. 8,324,421.

(51) Int. Cl.
*C07C 203/04* (2006.01)
*C07C 205/02* (2006.01)

(52) U.S. Cl.
USPC .............................. 558/485; 558/487; 568/712

(58) Field of Classification Search
USPC .................................... 558/485, 487; 568/712
See application file for complete search history.

(56) References Cited

PUBLICATIONS

Chavez, David E. Synthesis of an Energetic Nitrate Ester. Angewandte Chemie. 47(43). 8307-8309, (2008).*

* cited by examiner

*Primary Examiner* — Samantha Shterengarts
(74) *Attorney, Agent, or Firm* — Thomas S. O'Dwyer; James C. Durkis; John T. Lucas

(57) ABSTRACT

A process for the preparation of an energetic nitrate ester compound and related intermediates is provided.

6 Claims, 1 Drawing Sheet

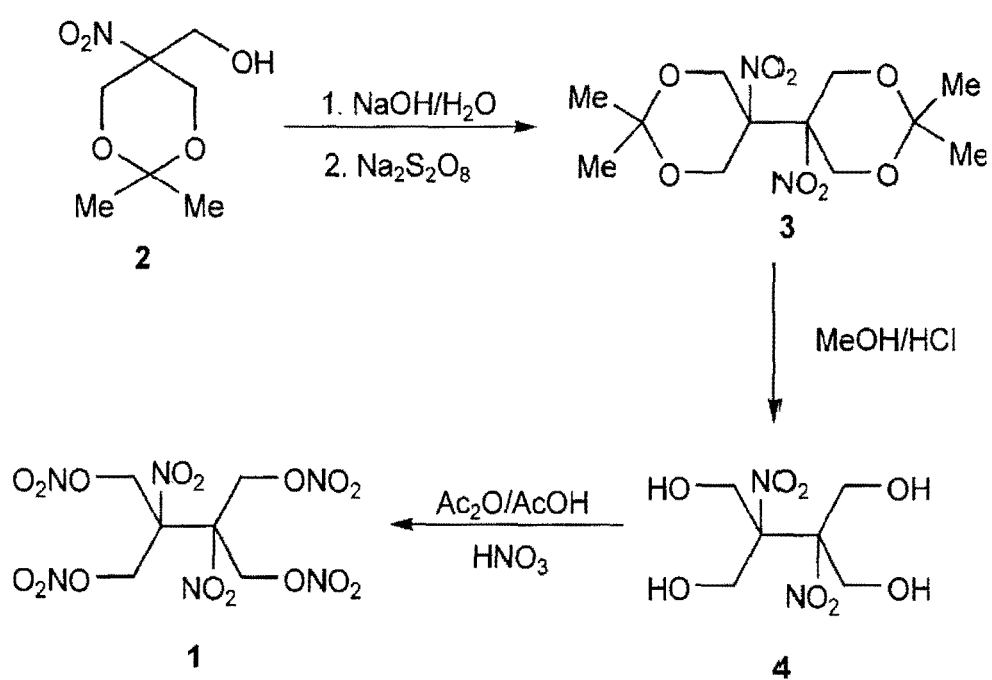

PROCESS FOR THE PREPARATION OF AN ENERGETIC NITRATE ESTER

This application is a divisional of application Ser. No. 12/566,331 filed Sep. 24, 2009, now U.S. Pat. No. 8,324,421 the entire contents of which are hereby incorporated by reference.

STATEMENT REGARDING FEDERAL RIGHTS

This invention was made with government support under Contract No. DE-AC52-06NA25396, awarded by the U.S. Department of Energy. The government has certain rights in the invention.

BACKGROUND OF INVENTION

The invention relates to energetic compounds and to the preparation of such compounds. More particularly, the invention relates to energetic nitrate esters.

Nitrate esters have been known as useful energetic materials since the discovery of nitroglycerin in 1846. The development of methods to increase the safety and utility of nitroglycerin by Alfred Nobel led to the revolutionary improvement in the use of nitroglycerin, in the form of dynamite, in explosive applications. Since then, many nitrate esters have been prepared and incorporated into military applications such as double-based propellants, detonators, and as energetic plasticizers. Nitrate esters have also been shown to have vasodilatory effects in humans and thus have been studied and used for treatments of ailments such as angina. The mechanism of the biological response towards nitrate esters has been elucidated recently.

Interestingly, many of the nitrate esters used for military purposes are liquids, e.g., ethylene glycol dinitrate and propylene glycol dinitrate. Pentaerythritol tetranitrate (PETN) is one of the only solid nitrate esters, besides nitrocellulose, that is used in explosive applications. Unfortunately, the melting point of PETN is above 100° C., and thus PETN must be pressed as a solid for use in detonator applications. A more practical material would be a melt-castable explosive, which would allow the simplification of manufacturing processes.

Herein is described the synthesis of an energetic nitrate ester that is a solid at ambient temperature, has a melting point range of 85-86° C., and has the highest density of any known nitrate ester composed of only carbon, hydrogen, nitrogen, and oxygen. The chemical, thermal, and sensitivity properties of this energetic nitrate ester are also described, as well as some preliminary explosive performance data.

SUMMARY OF INVENTION

The present invention provides an energetic nitrate ester shown by the formula:

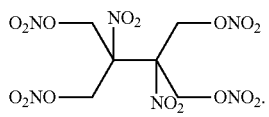

The present invention further provides a compound represented by the formula:

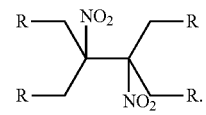

where each R group is independently selected from the group of hydroxide (—OH) and nitrate (—ONO$_2$).

The present invention further provides a process of preparing an energetic nitrate ester by reacting a mixture of a suitable dioxane compound and a sodium hydroxide solution with sodium persulfate to form an intermediate, admixing the intermediate with methanol, injecting the admixture with hydrochloric acid gas and maintaining the admixture for time sufficient to form a tetraol compound, and nitrating the tetraol compound to form the energetic nitrate ester. Variations of this process can yield various levels of nitration of the tetraol compound.

BRIEF DESCRIPTION OF THE DRAWINGS

FIG. 1 shows a schematic outline of the synthesis process of an energetic nitrate ester in accordance with the present invention.

DETAILED DESCRIPTION

The present invention is directed to an energetic nitrate ester, especially an energetic nitrate ester that is a solid at room temperature and has a melting point range that can facilitate melt casting of the material.

Referring to FIG. 1, a synthetic route to the energetic nitrate ester of the present invention is shown. Starting from the commercially available dioxane 2, the effects of concentration, oxidizer, and nitronate formation on the yield of 3 were initially examined. The amount of the potassium ferricyanide catalyst was also varied. Interestingly, it was found that increasing amounts of potassium ferricyanide led to reduction in the yield of the homocoupled product 3, whereas the yield of compound 3 increased in the absence of the catalyst. After optimization of temperature, concentration, and number of equivalents of base, the yield of the homocoupled product was eventually improved to 65%. With an improved method for the preparation of compound 3 in hand, the remaining two steps were further examined.

The tetraol product 4 was prepared by hydrolyzing the dimethyl ketal protecting group. Then, the nitrate ester molecule 1 was prepared by exhaustive further nitration of the tetraol 4. However, improvement in the yield of the oxidative coupling step was desired. Ketal deprotection was easily accomplished using methanolic HCl. Removal of the solvent led to compound 4 in good yield (85%). The nitration of the tetraol was found to provide the corresponding tetranitrate ester 1 in 85% yield by use of acetyl nitrate in acetic acid.

The tetranitrate ester compound 1 was characterized spectroscopically and thermally. The material begins to decompose at 141° C. with a decomposition energy release of 1818 Joules per gram (J/g). Interestingly, the material has a melting point range of 85-86° C. This property may allow the material to be used in melt-castable explosives applications. The heat of formation was measured to be −371 kilojoules per mole (kJ/mol) by combustion calorimetry using a Parr 6300 bomb calorimeter. The tetranitrate ester compound 1 can be recrystallized from a variety of solvents such as ethanol, isopropanol and chloroform. Large hexagonal crystals were obtained from ethanol.

X-ray crystallography was used to determine the crystal density of 1. A colorless thin plate of dimensions 0.40×0.10× 0.02 mm$^2$ was placed on a MiTeGen MicroMesh™ mount (available from MiTeGen LLC, Ithaca, N.Y.) using a small amount of Paratone-N oil (from Exxon). Data were collected using a three-circle platform diffractometer equipped with a SMART APEX II CCD detector (available from Bruker AXS, Inc., Madison, Wis.). The crystal density was determined to be 1.917 grams per cubic centimeter (g/cm$^3$), which makes compound 1 the most dense nitrate ester to date. Comparison of both the bond distances and bond angles of compound 1 with those of PETN show that certain bond lengths are slightly longer in compound 1 compared to the corresponding distances in PETN.

Additional description of the crystal structure and analysis of compound 1 are found within Chavez et al., Synthesis of an Energetic Nitrate Ester, Angew. Chem. Int. Ed. 2008, 47, 8307-8309, such description hereby incorporated by reference.

The sensitivity of material 1 towards destructive stimuli, such as impact, spark, and, friction was also investigated. It was determined that the sensitivity properties of 1 were very similar to those of pentaerythritol tetranitrate (see Table 1).

TABLE 1

|  | Impact[a] | Spark[b] | Friction[c] | DSC[d] |
| --- | --- | --- | --- | --- |
| comp1 | 2.7 J | 0.625 J | 74.5 N | 140° C. |
| PETN | 2.9 J | 0.625 J | 56.8 N | 160° C. |

[a]LANL type 12, 50% drop height, 2.5 kg.
[b]ABL spark threshold initiation level (TIL).
[c]50% load Bruceton up/down method.
[d]108° C. ramp rate.

Explosive performance calculations were performed with the CHEETAH thermochemical code (available from Lawrence Livermore National Laboratory (LLNL), Livermore, Calif.), using the experimental crystal density and measured heat of formation value as the input data. As displayed in Table 1, the performance of compound 1 is predicted to be equal to that of HMX, a well-characterized high-performance explosive. Unlike HMX however, nitrate ester 1 has a low melting point, which may provide a unique opportunity for melt-castable explosive components. Additionally, compound 1 offers the possibility of use as a high-energy plasticizer or double-base propellant ingredient. Further experiments are under way to fully characterize the explosive performance and properties of this novel nitrate ester. Additionally, compound 4 can serve as a synthon for new energetic materials and we are currently investigating the synthetic utility of 4.

The present invention is more particularly described in the following examples which are intended as illustrative only, since numerous modifications and variations will be apparent to those skilled in the art.

Cautionary note! Although no problems have occurred during the synthesis and handling of compound 1, the material is an explosive. Laboratories and personnel should be properly grounded and safety equipment such as Kevlar gloves, blast shields, and ear plugs are necessary, especially when working with large-scale reactions.

Example 1

The preparation of a first intermediate (compound 3) from a commercially available dioxane compound was as follows: Compound 2 (76.4 g, 0.40 mol), available from Sigma-Aldrich, St. Louis, Mo., was added to a solution of sodium hydroxide (32 g, 0.80 mol) in water (1 L) in a jacketed flask at 20° C. The reaction mixture was heated at 60° C. for one hour and then cooled to 20° C. Solid sodium persulfate (190 g, 0.80 mol) was added to the reaction mixture and the mixture stirred for 20 hours while maintaining the reaction at 20° C. During this time a white precipitate of 3 formed. The reaction mixture was then adjusted to pH>11, filtered, washed with cold water, and air dried to give 41.6 g of 3 (65%). The product was identical in all respects to that previously reported.

Example 2

The preparation of compound 4 was as follows: Compound 3 (25.6 g, 0.08 mol) was added to methanol (240 mL). The reaction mixture was stirred while HCl gas was bubbled into the reaction mixture. When dissolution was complete, the HCl addition was stopped, the reaction vessel was stoppered, and the reaction mixture stirred for 48 hours. During this time, the color of the reaction mixture turned from amber to dark brown. The volatile components were then removed and the residue was triturated with warm chloroform and filtered to provide 8.1 g of 4 (85%). M.p. 100-102° C.; IR (KBr): ν=3596, 3284, 2975, 2913, 2888, 1482, 1463, 1408, 1385, 1341, 1303, 1255, 1230, 1159, 1135, 1069, 1035, 994, 930 cm$^{-1}$; $^1$HNMR (CD$_3$CN, 300 MHz): δ=3.35 (brs, 4H), 4.22 ppm (m, 8H); $^{13}$CNMR (CD$_3$CN, 100 MHz): 8=61.18, 96.38 ppm. Elemental analysis calcd for C$_6$H$_{12}$N$_2$O$_8$: C, 30.01; H, 5.04; N, 11.66. found: C, 30.38; H, 5.29; N, 11.35.

Example 3

The preparation of compound 1 was as follows: Acetic acid (50 mL) and acetic anhydride (50 mL) were added to a 200 mL jacketed flask. The solution was then cooled to 0° C. and nitric acid or HNO$_3$ (34 g, 98%) was added dropwise while maintaining the reaction temperature below 5° C. The reaction was allowed to stir for 20 minutes and 4 (12 g, 0.05 mol) was added portionwise. After stirring the mixture for 2 hours at 0° C., the temperature was raised to 208° C. over one hour and then stirred at 208° C. for an additional hour. The reaction mixture was then poured into 200 mL of ice-water and stirred. The white solid was filtered, washed with water, and air dried to give of crude 1 (20 g). This material was then recrystallized from isopropanol to give 18 g of 1 (85%). M.p. 85-86° C.; IR (KBr): ν=3045, 3028, 2982, 2927, 1658, 1583, 1491, 1465, 1450, 1390, 1371, 1334, 1287, 1156, 1099, 1056, 1022, 995, 898, 854 cm$^{-1}$; $^1$HNMR (CDCl$_3$, 300 MHz): 5=56 ppm (s, 8H); $^{13}$CNMR (CDCl$_3$, 100 MHz) δ=68.57, 90.73 ppm. Elemental analysis calcd for C$_6$H$_8$N$_6$O$_{16}$: C, 17.15; H, 1.92; N, 20.00. found: C, 17.48; H, 2.20; N, 19.86.

Although the present invention has been described with reference to specific details, it is not intended that such details should be regarded as limitations upon the scope of the invention, except as and to the extent that they are included in the accompanying claims.

What is claimed is:

1. A process for preparing an energetic nitrate ester comprising:
   reacting a mixture of a suitable dioxane compound and a sodium hydroxide solution with sodium persulfate to form an intermediate;
   admixing the intermediate with methanol and injecting the admixture with hydrochloric acid gas;
   maintaining the admixture for time sufficient to form a tetraol compound; and, nitrating the tetraol compound to form the energetic nitrate ester.

2. A tetraol compound prepared in accordance with claim 1 and represented by the formula:

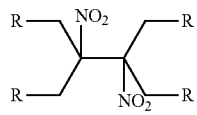

where each R group is independently selected from the group of hydroxide (—OH) and nitrate (—ONO$_2$).

3. The compound of claim 2 wherein the R groups consist of one hydroxide group (—OH) and three nitrate groups (—ONO$_2$).

4. The compound of claim 2 wherein the R groups consist of two hydroxide groups (—OH) and two nitrate groups (—ONO$_2$).

5. The compound of claim 2 wherein the R groups consist of three hydroxide groups (—OH) and one nitrate group (—ONO$_2$).

6. The nitrated tetraol compound of claim 1 wherein said compound comprises:
1,4-butanediol,2,3-dinitro-2,3-bis[(nitrooxy)methyl]-,1,4-dinitrate.

* * * * *